United States Patent [19]
Pungor, Jr. et al.

[11] Patent Number: 5,864,021
[45] Date of Patent: Jan. 26, 1999

[54] METHOD AND APPARATUS FOR THE PRODUCTION OF TGF-β AND PURIFIED TGF-β COMPOSITIONS

[75] Inventors: Erno Pungor, Jr.; Eirik Nestaas, both of Foster City, Calif.

[73] Assignee: Berlex Laboratories, Inc., Wayne, N.J.

[21] Appl. No.: 838,729

[22] Filed: Mar. 16, 1992

Related U.S. Application Data

[63] Continuation-in-part of Ser. No. 405,695, Sep. 11, 1989, Pat. No. 5,043,431, filed as PCT/US90/05098, Sep. 10, 1990.

[51] Int. Cl.$^6$ ....................................................... C07K 3/00
[52] U.S. Cl. .......................... 530/416; 530/399; 530/412
[58] Field of Search ..................................... 530/399, 416, 530/412

[56] References Cited

U.S. PATENT DOCUMENTS

| | | | |
|---|---|---|---|
| 4,332,717 | 6/1982 | Kanaoka et al. | 424/108 |
| 4,427,580 | 1/1984 | Kinsella et al. | 530/371 |
| 4,444,760 | 4/1984 | Thomas et al. | 424/177 |
| 4,751,078 | 6/1988 | Nagabhushan et al. | 530/416 |
| 4,894,439 | 1/1990 | Dorin et al. | 530/351 |
| 4,897,464 | 1/1990 | Vallee et al. | 530/350 |
| 4,931,548 | 6/1990 | Lucas et al. | 530/399 |
| 5,043,431 | 8/1991 | Pungor, Jr. et al. | 530/399 |

FOREIGN PATENT DOCUMENTS

| | | |
|---|---|---|
| 0 323 842 | 7/1989 | European Pat. Off. . |
| 88/03807 | 6/1988 | WIPO . |

OTHER PUBLICATIONS

Massague, "Type B Transforming Growth Factor from Feline Sarcoma Virus–Transformed Rat Cells," *The J. of Biolo Chem*, vol. 259, No. 15,pp. 9756–9761, 1984.

Van Den Dijnden–Van Raaij, "Purification of a Growth Factor Related to Platelet Derived Growth Factor and a Type B Transforming Growth Factor Secreted by Mouse Neuroblastoma Cells," *Biochem J.*, vol. 257, pp. 375–382, 1989.

Assoian et al., "Transforming Growth Factor–B in Human Platelets,," *Journal of Biological Chem*, vol. 258, No. 11, Jun. 10, pp. 7155–7160, 1983.

Frolik et al., "Purification and Initial Characterization of a Type B Transforming Growth Factor from Human Placenta," *Proc. Natl Acad Sci*, vol. 80, pp. 3676–3680, Jun. 1983.

Roberts et al, "Purification and Properties of a Type B Transforming Growth Factor from Bovine Kidney," *Biochemistry*, vol. 22, pp. 5692–5698, 1983.

Okada et al., *J. Biochem*, 106:304–310 (1989).

*Primary Examiner*—Shailendra Kumar
*Attorney, Agent, or Firm*—Millen, White, Zelano, & Branigan, P.C.

[57] ABSTRACT

Transforming growth factor β (TGF-β) is produced in relatively large quantities and at a relatively high purity by fermentation in a perfusion microcarrier reactor. Conditioned media from the reactor is first treated to provide the active form of TGF-β and subsequently purified by cation exchange chromatography followed by hydrophobic interaction chromatography. Optionally, nucleic acids complexed with the TGF-β may be removed while the protein is bound to the cation exchange resin. Purified TGF-β1 compositions have a specific activity above $10^7$ U/ml.

5 Claims, 4 Drawing Sheets

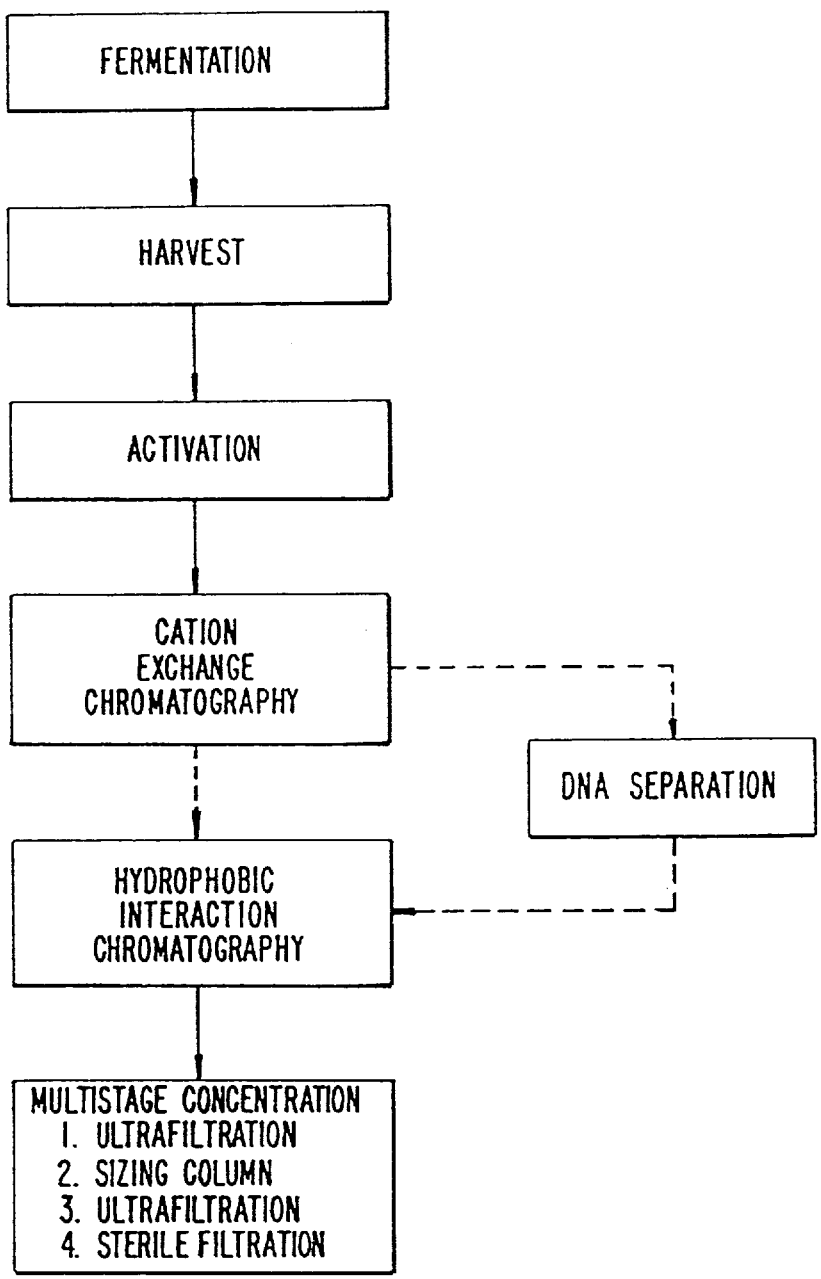
FIG._1.

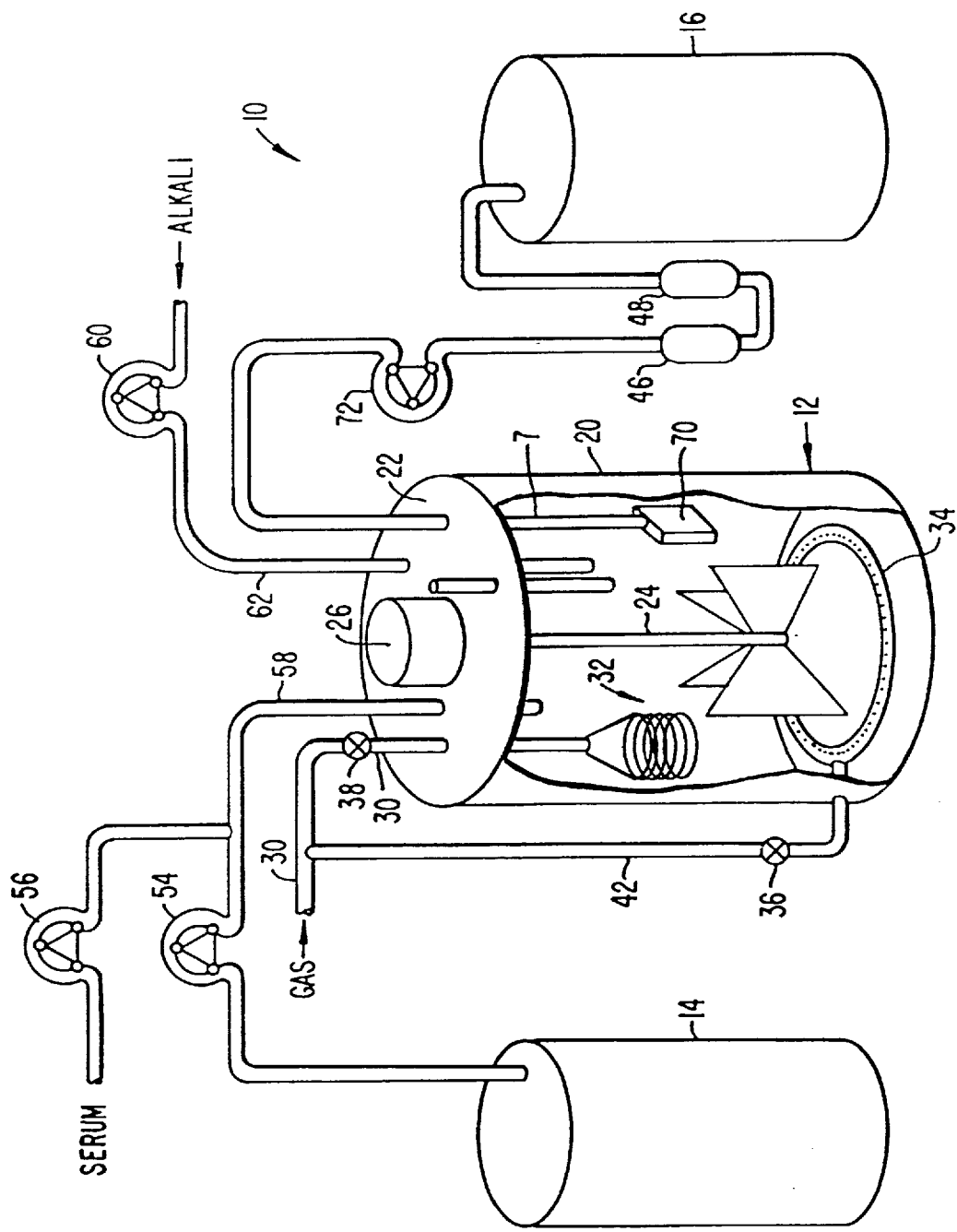
FIG._2.

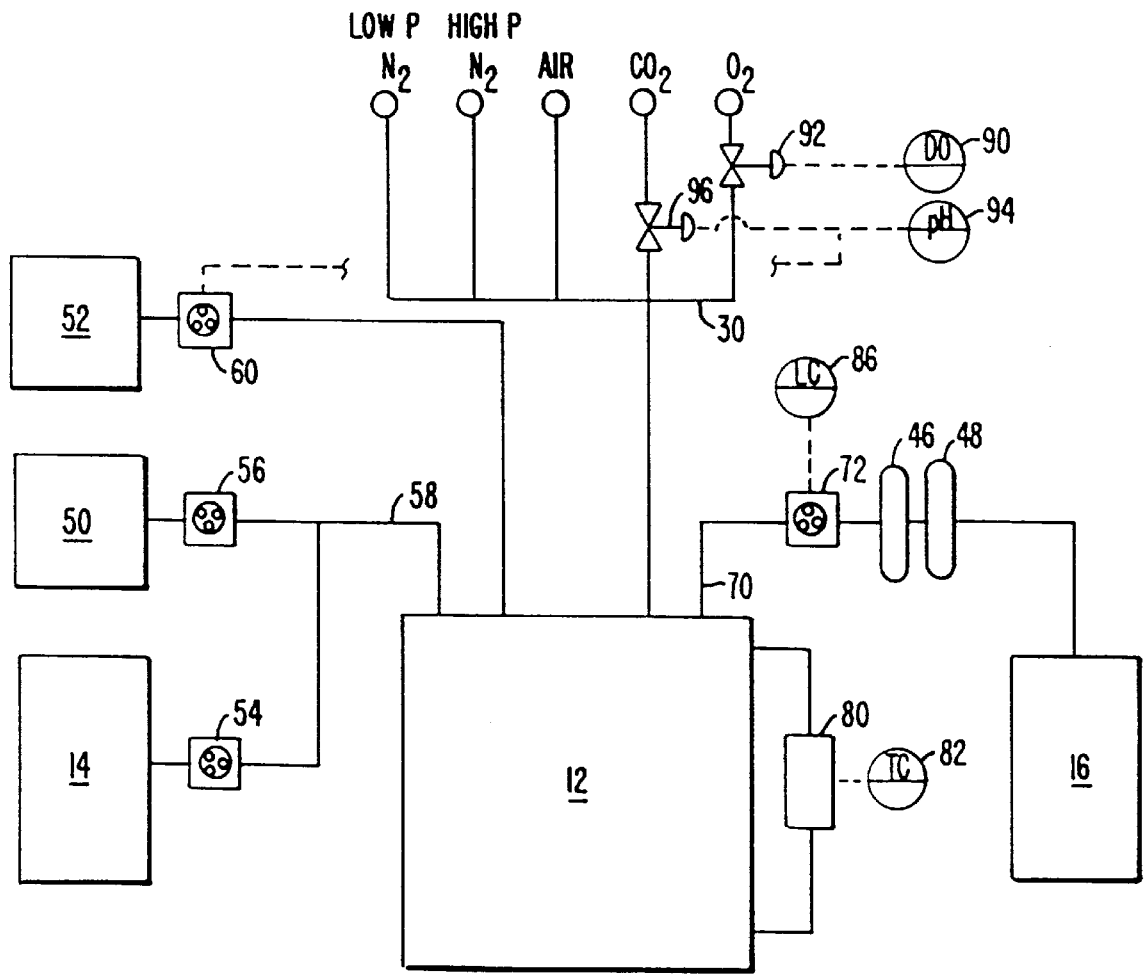
FIG._ 3

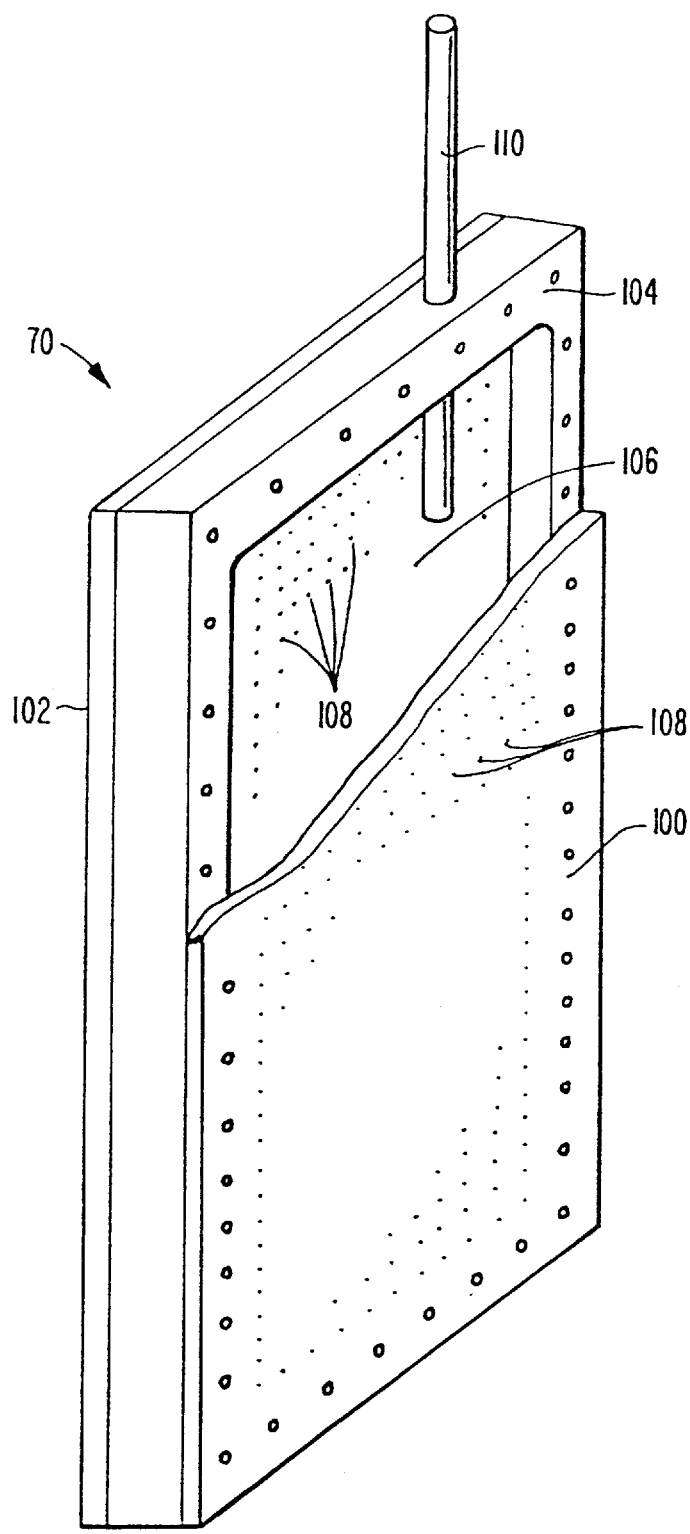
FIG._4.

METHOD AND APPARATUS FOR THE PRODUCTION OF TGF-β AND PURIFIED TGF-β COMPOSITIONS

This application is a continuation-in-part application of U.S. application Ser. No. 07/405,695, filed Sep. 11, 1989, now U.S. Pat. No. 5,043,431, which application is designated as a U.S. National Phase under PCT/US90/05098, filed 10 Sep. 1990.

BACKGROUND OF THE INVENTION

1. Field of the Invention

The present invention relates generally to methods for production of transforming growth factor β and, more particularly, to methods for the large scale fermentation and purification of transforming growth factor β from mammalian cell culture.

Transforming growth factor β (TGF-β) is a multifunctional peptide shown to be active in regulating a wide variety of both normal and neoplastic cell types. It is a 25,000 MW homodimer consisting of two 12,500 subunits bound together by nine disulphide bridges and is synthesized as a 391 amino acid molecule comprised of a 29 amino acid leader peptide and a 362 amino acid latent precursor. Mature, active TGF-β consists of the C terminal 112 amino acids of the latent peptide. The precise means of physiological activation is unknown, and the mature peptide is not glycosylated. There are, however, three potential N-linked glycosylation sites in the precursor portion of the protein, all of which appear to be used.

At least five different TGF-β's have been described, including TGF-β 1,2,3, and 4. The sequence homology between the different forms of the mature TGF-β peptide ranges from 64–82%. The sequence homology between the precursor sequences is somewhat lower averaging about 40%. All are functionally homologous although there is some difference in TGF-β receptor binding properties.

TGF-β has been shown to be an effective cell growth promoter, particularly with epithelial cells, and the use of TGF-β as a wound healing agent has been demonstrated.

It would therefore be desirable to provide methods for producing TGF-β in relatively large quantities. It would be particularly desirable to provide methods for both fermentation and purification of TGF-β from mammalian cell culture. The fermentation procedures should be able to produce large quantities of TGF-β, preferably at least 1 mg/L-day, and the purification procedures should be able to purify such quantities to a very high degree, preferably 99% purity or above.

2. Description of the Background Art

Mature TGF-β has been purified on a laboratory scale from the conditioned media of producer cell lines. A six step purification procedure including lyophilization, acid resuspension, gel filtration, reverse phase high pressure liquid chromatography (HPLC), SDS-polyacrylamide gel electrophoresis, and extraction is described in Massague (1984) J. Biol. Chem. 259:9756–9761. An eight step purification procedure including lyophilization, acid extraction, dialysis, lyophilization, gel filtration, cation exchange HPLC, and reverse phase HPLC is described in Van den Eignden-Van Raaij et al. (1989) Biochem. J. 257:375–382. Mature TGF-β has also been purified from several tissues and whole cells, generally employing a four step process including extraction with acid and ethanol, gel filtration, cation exchange, and reverse phase HPLC. See, e.g., Assoian et al. (1983) J. Biol. Chem. 258:7155–7160; Frolik et al. (1983) Proc. Natl. Acad. Sci. USA 80:3676–3680; and Roberts et al. (1983) Biochem. 22:5692–5698. Copending application Ser. No. 07/184,519 describes a fermentation system similar to that employed in the present invention.

SUMMARY OF THE INVENTION

According to the present invention, TGF-β is produced by fermentation of a mammalian cell line transformed to overproduce TGF-β. The cells are grown on a microcarrier matrix in a perfusion culture, and the TGF-β is secreted into the culture medium. The resulting conditioned media is harvested, and the latent precursor TGF-β is activated, typically by exposure to acid or heat. The resulting active TGF-β is present in the conditioned media at a relatively low concentration, usually substantially below 1% of the protein present.

The active TGF-β in the conditioned media is then purified by cationic ion exchange followed by hydrophobic interaction chromatography under conditions selected to provide a highly purified product. More specifically, the active TGF-β in the conditioned media is applied to a cation exchange matrix under conditions resulting in substantially complete binding of the TGF-β to the matrix. The TGF-β is then selectively eluted and the fraction containing the TGF-β is collected. The collected fraction is then applied to the hydrophobic interaction matrix, and the TGF-β is again selectively eluted, providing for a high purity, typically above 95%, preferably above 99%. The resulting product may then be concentration by conventional techniques, such as ultrafiltration and sizing column chromatography.

In a particular aspect of the present invention, nucleic acids complexed to the TGF-β may be removed to further enhance the product purity. Nucleic acids are highly undesirable contaminants, particularly when the TGF-β is intended for human therapeutic use. Surprisingly, the TGF-β may be released from the nucleic acid-TGF-β complexes while the TGF-β is bound to the cation exchange matrix. Initial binding of the TGF-β to the ion exchange matrix is effected under conditions of low ionic strength and relatively neutral pH. The nucleic acids are released by raising the pH or slightly increasing ionic strength in the mobile phase of the column sufficiently to disrupt the nucleic acid complexes while leaving the TGF-β bound in the column.

This approach for removing nucleic acids from protein-nucleic acid complexes is generally applicable to a wide variety of proteins and not limited to TGF. The removal may be effected by first binding the protein-nucleic acid complex to a cation exchange matrix, preferably a strong cation exchange resin having a high capacity and ligand density. The complexes are bound under conditions of low to moderate ionic strength and moderate pH. The nucleic acids may be released from the complexes by applying to the matrix a mobile phase with a pH sufficiently increased or ionic strength slightly increased to disrupt the binding between the nucleic acids and the protein. By maintaining substantially the same ionic strength, the binding between the protein and the cationic matrix is maintained. Thus, the nucleic acids may be removed from the protein while the protein remains bound to the resin. The protein may subsequently be eluted from the cationic matrix by conventional elution methods, typically by increasing the ionic strength.

In a second particular aspect of the present invention, the conditioned media may be harvested from the fermenter using a perforated-screen baffle assembly which is suspended in the fermenter. The perforated screen has a smooth, polished surface which has been found to remain clean and free from fouling even during extensive use. The perforations in the screen are sized at from 80–120 μm, which size allows free collection of the conditioned medium with the desired proteins, but which is has been found to be effective to exclude virtually all intact cells and microcarrier beads. Surprisingly, the holes in the perforated screen are not plugged by the cells, cellular debris, or the microcarriers.

In a third particular aspect of the present invention, purified TGF-β1 compositions having a specific activity above $10^7$ U/mg (as defined hereinbelow), preferably above $1.5 \times 10^7$ U/mg, more preferably above $2 \times 10^7$ U/mg are provided. The purified TGF-β1 compositions are preferably produced by the purification process of the present invention described above.

BRIEF DESCRIPTION OF THE DRAWINGS

FIG. 1 is a block diagram illustrating the processing steps of the method of the present invention.

FIG. 2 is a schematic illustration of a cell perfusion culture system suitable for performing the fermentation step of the present invention.

FIG. 3 is a block diagram illustrating the various subsystems and control systems associated with the cell perfusion culture system of FIG. 1.

FIG. 4 illustrates a conditioned media collection baffle useful in the cell perfusion culture system of the present invention.

DESCRIPTION OF THE SPECIFIC EMBODIMENTS

Referring now to FIG. 1, TGF-β is produced by fermenting a mammalian cell line capable of secreting the TGF-β into a conditioned media. The conditioned media is harvested, and the TGF-β is activated and separated from other proteins and contaminants by first applying the conditioned media to a cation exchange media, followed by selective elution of the TGF-β from the matrix. Optionally, nucleic acids may be removed from TGF-β-nucleic acid complexes while the TGF-β remains bound to the cationic ion exchange matrix. The TGF-β fraction obtained by selective elution from the cationic ion exchange matrix is then applied to a hydrophobic interaction matrix, where a selective elution from the matrix provides a second level of purification. The purified TGF-β is next concentrated by conventional techniques, such as ultrafiltration and sizing column chromatography.

A system 10 (FIGS. 2 and 3) suitable for the large-scale fermentation of mammalian cell line capable of producing TGF-β includes a reactor vessel containing a microcarrier matrix upon which the cell line may be grown, a culture media supply system, a gas supply system, a conditioned media removal system, and several subsystems for controlling temperature, level, pH, dissolved oxygen, and agitation speed within the reactor. The interconnections among the various systems and subsystems are illustrated in FIGS. 2 and 3.

1. Reactor Vessel

A cell perfusion culture system 10 includes a reactor vessel 12, a culture media tank 14, and a condition media tank 16. The reactor vessel 12 is typically a cylindrical tank 20 which is sealed at its upper end by a head plate 22. The head plate provides a plurality of aseptic penetration ports for the insertion of piping, sensors, and the like. The reactor vessel 12 may be a standard bacterial fermenter of a type which is commercially available. The volume of the reactor vessel will typically be in the range from about 1 to 10,000 liters, usually being in the range from about 10 to 1,000 liters.

Reactor vessel 12 will include an agitator capable of providing low-shear mixing of the vessel contents. Particularly suitable is a large-blade marine impeller 24 which provides both horizontal and vertical mixing at low rotational speeds. Alternatively, a vertically oscillated perforated plate (not illustrated) provides sufficient vertical mixing in improved aeration of the culture media with minimum cell damage. As illustrated, the impeller 24 is driven by an electric motor 26 mounted on the head plate 22.

The reactor vessel 12 will contain microcarriers in a suitable culture media for growing the mammalian cells of interest. The microcarriers are small particles, typically spherical, having dimensions in the range from about 50 to several hundred microns. The microcarriers define a surface suitable for cell attachment and growth and will generally be suspended in the reactor vessel 12 by action of the agitator. In this way, nutrients are delivered to the cells and metabolites removed from the cells in a highly efficient manner while maintaining the cell attachment necessary for growth. The composition of the microcarriers is not critical, and a variety of materials are suitable, including natural polymers, such as dextran, and synthetic polymers, such as methacrylates, styrene, and the like.

The reactor vessel 12 will also include a system for heating and cooling the vessel contents. Conveniently, the heating/cooling system may be a fluid jacket (not illustrated) for receiving a heat exchange medium, described in more detail hereinafter. Alternatively, the heating/cooling system may comprise immersed coils (not illustrated) for receiving the heat exchange medium. The design of suitable heating/cooling systems is conventional and need not be described further.

A gas supply manifold 30 (FIG. 2) includes high and low pressure nitrogen connections, as well as sterile air, oxygen, and carbon dioxide connections. Oxygen and carbon dioxide are supplied to the reactor vessel 12 through a gas permeable membrane 32 (FIG. 1) which is immersed within the culture media during operation of the system. Optionally, both the oxygen and carbon dioxide are connected to a sparging ring 34 which is generally at the bottom of the reactor 12. Isolation valves 36 and 38 may select for gas addition through either or both of the gas permeable membrane 32 and sparging ring 34. As will be described in more detail hereinafter, gas introduction will initially be effected through the gas permeable membrane 32 while the culture is being expanded. During the initial stages of expansion, the cells growing on the microcarrier matrix are particularly sensitive to shear damage which can arise as a result of bubbling from the sparger 34. Once high density culture is reached, however, the oxygen demand of the culture increases substantially and the sensitivity to shearing decreases. The gas introduction by sparging becomes desirable at that point in order to provide sufficient oxygen to support the high density culture.

A suitable gas permeable membrane can be constructed from a coil of silicone rubber tubing which is wound around a cylindrical support gauge. Conveniently, the tubing and support gauge are suspended from gas conduit 40 which penetrates through an aseptic port and head plate 22. Sparging ring 34 is supplied by a second gas conduit 42 which branches from the manifold 40 and penetrates through the side wall of the cylindrical tank 20.

2. Culture Media Feed System

The culture media feed system includes the culture media tank 14, a serum pre-mix tank 50, and an alkali feed tank 52. The culture media is fed from tank 14 to reactor vessel 12 by a suitable sterile pump 54, typically a peristaltic pump. Similarly, the serum premix is fed from tank 50 through a second sterile pump 56, which will again typically be a peristaltic pump. Conveniently, although not necessarily, the feedline from both the culture media tank 14 and serum premix tank 50 are combined into a single inlet conduit 58 which penetrates the head plate 22 through an aseptic port.

Alkali from tank 52 is transferred by sterile pump 50, again which will usually be a peristaltic pump. The alkali will be fed through a separate inlet conduit 62 which extends through an aseptic port in the head plate 22 and terminates within the tank 20 at a level which will typically be beneath the level of culture media during operation.

3. Conditioned Media Recovery System

Provision must be made for recovering the conditioned media from the reactor vessel 12 without the carryover of microcarrier beads, cells, or cellular clumps. Conveniently, such recovery and separation may be effected by conventional elutriation tube which provides for a relatively high degree of separation of microcarrier beads, cells, cellular clumps, and the like.

Preferably, however, the present invention will employ a collection baffle assembly 70 suspended from the head plate 22 by a connection tube 71. The collection baffle 70, best illustrated in FIG. 4, comprises a pair of collection screens 100 and 102 secured to opposite faces of a spacer member 103. The spacer member 104 includes an open interior 106 which, together with the screen plates 100 and 102, defines an interior collection plenum. The screen plates 100 and 102 include a plurality of very small apertures 108 formed therethrough to allow the collection of conditioned media within the plenum, while excluding microcarrier beads, cells, and cellular clumps. A collection tube 110 extends into the interior 106 of the collection baffle 70. The collection baffle may be connected to collection tube 71 by any convenient means. In order to effectively exclude the cellular materials and the microcarrier beads, while allowing an adequate inflow of the conditioned medium at a moderate pressure drop, it has been found that apertures having a size in the range from about 80 $\mu$m to 120 $\mu$m are effective. Preferably, the apertures will be circular and may be formed by conventional electromachining processes. In order to avoid plugging and fouling of the collection plenum, it is desirable that the exposed surface of each screen plate 100 and 102 be very smooth, preferably being polished.. The use of screen plates having such polished surfaces and apertures in the size range described above has been found to allow for collection over very long periods of time without substantial plugging or fouling.

Although illustrated as a pair of flat plates, it will be appreciated that the collection baffle may have a wide variety of geometries. For example, it would be possible to form a collection plate into a cylindrical geometry where the collection plenum is located within the interior of the cylinder. In that case, it would be necessary to provide only top and bottom plates to complete the isolation of the plenum.

4. System Control

The control system of the present invention may comprise a plurality of discrete automatic controllers or, preferably, a single digital control system which may conveniently be a microprocessor-based control system.

The primary system parameters which are measured and controlled include temperature, level (or volume), pH, and dissolved oxygen of the culture media within the reactor 12. Suitable sensors (not illustrated) will be provided for each of these parameters, typically by inserting a sensor probe through an aseptic port in the head plate 22. Numerous sensors suitable for measuring each of these parameters are commercially available which may be easily adapted to the system of the present invention. The outputs of the sensors will be fed to the control system which will then effect adjustments in the parameter (as described below) based on normal feedback control algorithms.

Secondary system variables which are controlled include the flow rates of culture media from tank 14 and serum premix from tank 50 into reactor 12 (which are conveniently controlled by adjusting the speeds of pumps 54 and 56, respectively), the agitator 24 speed, the oxygen pressure within the membrane 32, the pressure within the reactor head (i.e., the volume above the liquid media surface), the precise oxygen supply composition, microcarrier addition rate, and growth media perfusion rate. The control of the secondary variables will generally not be based on feedback from measured parameters, but rather will be based on the observed cell growth characteristics within the vessel. As will be described in more detail hereinafter, the serum will be added at a higher concentration during the initial stages of operation when the cell culture is being expanded. Similarly, the feed rate of culture media will be controlled by the operator based on a number of observed operating parameters of the system.

Temperature control is achieved by a heater/chiller unit 80 which circulates a heat exchange medium, typically water, through a fluid jacket or other suitable heat exchanger on reactor vessel 12. The temperature and/or flow rate of the heat exchange medium is controlled by temperature controller 82 to maintain a substantially constant temperature within the reactor 12.

Level of the conditioned media within reactor 12 is controlled by level controller 86 which adjusts the speed of outlet pump 72 which, of course, adjusts the volume rate at which the condition media is drawn from reactor 12. Thus, any changes in the inlet flow of culture medium caused by changes in the throughputs of pump 54 and/or 56 (as selected by the operator) will be automatically compensated for by the level controller 86.

Dissolved oxygen is controlled (usually to a level of about 50% $CO_2$) by a dissolved oxygen controller 90 which adjusts a control valve 92 which modulates the flow rate of oxygen in through the gas permeable membrane 32 and sparging ring 34. When the maximum flow capability of the sparging ring 34 is insufficient to increase the dissolved oxygen concentration to the desired level, flow through the membrane 32 will be commenced.

The pH control is effected by pH controller 94 which adjusts a control valve 96 and pump 60. The control valve 96, in turn, adjusts the inlet flow rate of carbon dioxide, while pump 60 controls the inlet flow rate of alkali 52.

Daily glucose assays will be taken with a commercially available glucose meter. The perfusion rate will be increased by a fixed amount, usually about 0.5 culture volumes/day so long as the glucose concentration remains below a desired level, typically about 1.5 mg/ml. The maximum perfusion rate will be about 2 culture volumes/day.

In addition to the glucose assays, sterility tests, cell counts, cell viability tests, and microscopic examination of the cells will be performed at least once a day for each reactor. The volume of culture media available in tank 14 and remaining capacity of conditioned media tank 16 should also be checked periodically to assure the continuous operation of the system.

5. Culture Media

The culture media comprises a base media suitable for mammalian cell growth, such as WEC medium. For the inoculation growth phase, the base media will usually be supplemented with a serum source, typically fetal bovine serum (FBS), present at a concentration in the range from about 1 to 10% by weight, usually being present at about 2 to 5% by weight. During the perfusion growth phase, the FBS concentration is usually maintained at a lower concentration, typically being in the range from about 0.1 to 1%, usually being about 0.5%. During both growth phases, the serum source should be treated to remove proteolytic and other enzymes, for example by contacting the serum with lysine-Sepharose as described in co-pending, commonly assigned U.S. Ser. No. 167,061, filed on Mar. 11, 1988, the disclosure of which is incorporated herein by reference. The use of such "scrubbed" serum helps minimize degradation of the TGF-$\beta$ secreted into the conditioned media and further effects the removal of serum proteins which would otherwise co-purify with the TGF-$\beta$. Other growth factors may also be added, such as glutamine (optimally at 400 mg/L). Aprotinin (usually at 0.1 to 10 kIU/ml and preferably at 1 to 5 kIU/ml) may be added as a protease inhibitor to further protect the product released into the conditioned media.

6. Cell Lines

Cell lines suitable for use in the present invention include mammalian cell lines capable of adherent growth on microcarrier beads. Usually, the cell lines will also be capable of growth in suspension culture to facilitate propagation of the initial microcarrier inoculum. Particular cell lines which meet these requirements include Chinese hampster ovary (CHO) cell lines.

A particularly preferred CHO cell line is B-3-2000, clone 17, which is described in Dentry et al. (197) Mol. Cell Biol. 7:3418–3427.

7. Start-Up

Prior to operation, all components of the reactor system 10 will be sterilized, typically by autoclaving. Conveniently, lines to and from the reactor vessel 12 will be covered with narrow pore (0.2 $\mu$m) hydrophobic filters which will allow steam penetration without allowing subsequent entry of microorganisms. The reactor should be autoclaved with liquid covering the various sensor probes, and a vacuum should be drawn on the reactor to prevent air pocket entrapment which can interfere with steam penetration.

The liquid in the vessel 12 is removed to the extent possible through a sample line (not illustrated) and fresh culture media from vessel 14 is provided. A desired amount of the serum premix is also added and an anti-foam controller (not illustrated) is started. The reactor is allowed to agitate for one or two days at 37° C. in 100% dissolved oxygen as a sterility test. If the culture medium remains sterile at the termination of the test, it is ready for inoculation.

The reactor vessel 12 may be inoculated by either of two procedures, the first employing cells attached to microcarriers and the second employing cells in suspension. In both cases, the inoculum is expanded from a master working cell bank of frozen aliquots, according to standard cell culture techniques. Once a sufficiently large population is obtained, the reactor vessel 12 may be inoculated.

Using the microcarrier inoculation procedure, a spinner culture of microcarrier particles is allowed to grow to a density of about 1×10$^6$ cells/ml. The amount of inoculation culture required will vary depending on the volume of the reactor. Typically, the ratio of inoculum volume to reactor volume will be in the range from about 1:10 to 1:20. Care must be taken to assure that transfer of the spinner culture does not introduce contaminating microorganisms into the reactor vessel 12. Typically, microcarriers are transferred by pressurizing the spinner culture vessel while supplying agitation to keep the microcarriers in suspension. The inoculum is then transferred through a transfer tube by overpressure to the reactor.

To utilize a suspension inoculum, reactor vessel 12 is filled with a calcium-free growth media. A suspension of cells is obtained by trypsinization from roller bottles and transfer is achieved using a sterile aspirator flask by overpressure. Cells are transferred to the reactor at a final reactor concentration in the range from about 10$^5$ to 10$^6$ cells/ml.

8. Expansion of the Culture to High Density

After inoculation with either the microcarrier or free-cell suspension, the cell culture will be expanded to production density, typically in the range from about 10$^6$ to 3×10$^7$ cells/ml. In the case of microcarrier inoculation, the culture is allowed to grow on the initial charge of microcarriers without the addition of fresh media, until the cell density reaches a predetermined intermediate level, typically in the range from about 1 to 2×10$^6$ cells/ml or until the glucose residual in the culture media decreases to less than about 25% of its initial level. In the case of a free-cell suspension inoculum, free cell density is allowed to increase without addition of fresh culture media until the cell density reaches about 10$^6$ cells/ml. After that density is reached, sufficient calcium is added to the culture medium to render the cells adherent and microcarriers are added, typically to a concentration of about 1 gram of beads per liter of culture medium. In a short time, typically about 24 hrs., the cells attach to the beads, and the remaining expansion procedure is identical for both microcarrier and free cell suspension inoculums.

After the desired cell density on microcarriers is achieved, perfusion of fresh media supplemented with serum premix is initiated. Typically, the concentration of serum in the fresh media will be in the range from about 2% to 10% by weight, more typically in the range from about 3% to 8% by weight, and normally being about 5% by weight. Initially, the perfusion rate will be in the range from about 0.25 to 0.75 culture volumes/day, typically being about 0.5 culture volumes/day. As the cell growth increases, the perfusion rate is increased to a final rate in the range from about 1.5 to 2.5 culture volumes/day, typically over a period of about 2 to 10 days. During the expansion, sterile, pre-equilibrated microcarriers are added to the reactor to maintain the microcarrier to cell density ratio in the range from about 0.5 to 1.0 grams of beads to 10$^9$ cells. Conveniently, the beads are added to the reactor using an aspirator through the sample line.

9. Production Phase

After cell density has reached the production level, the serum addition to the fresh culture medium will be reduced, typically to a concentration in the range from about 0.1 to 0.5 weight percent.

The culture in production phase requires little attention. Additional culture media, serum, and alkali need to be provided as the supply tanks are depleted. Samples of the condition media should be analyzed at least once a day to assure that production continues free from contamination.

10. Batch Production

As an alternative to the continuous production protocol described above, the conditioned medium may be produced by a batch or semi-continuous procedure where the agitator in the reactor vessel is periodically stopped, and the microcarrier beads allowed to settle to the bottom of the reactor. The culture supernatant is rapidly pumped out, typically through the sample line or by adjusting the position of the elutriation tube. Pre-heated fresh media is then pumped back into the reactor in an amount sufficient to restore the operating level. The culture may then be continued, either with or without perfusion, until the next batch of media is withdrawn.

With the method just described, substantially all of the cell culture can be maintained in the reactor in a viable state even while withdrawing most of the culture media. Production of the desired polypeptide is then reinitiated by adding the fresh media. Generally, the batch production method will not be preferred over the continuous production method.

11. Activation

After harvesting, the conditioned media may be stored at room temperature for a period of up to about 10 days without pH adjustment. At any time during this period, the precursor TGF-β may be activated, typically by acid treatment followed by heat treatment. Acid treatment may be effected by adjustment of the pH of the condition media to the range from about 2.5 to 3.0 with a strong mineral acid, such as 5M HCL. The acidified condition media is left at the reduced pH for a period of approximately 24 hours, and the pH then adjusted back to the range from about 5 to 7, preferably to about 6, prior to initiation of the purification procedures. Heat activation of the acidified product may be accomplished by batch heating or heating in a continuous flow system, where the residence time at high temperature (40° to 80° C.) can range from about 10 minutes to 8 hours.

After activation, the TGF-β will typically be present in the condition medium at a concentration less than about 1%, usually being less than about 0.5%, and frequently being 0.1% or below.

12. Cation exchange Chromatography

After pH adjustment to the range from 5 to 7, preferably to about 6, the activated TGF-β in the conditioned media is applied to a cation exchange matrix (usually in the form of a column) under conditions selected to provide substantially complete binding of the TGF-β. While other proteins will also be bound, the initial binding stage provides a first level of separation as a number of the contaminating proteins in the conditioned media will be unable to bind to the matrix and thus will flow through the matrix. The TGF-β is further purified by selective elution from the matrix, where the elution may be accomplished by either stepwise elution or linear gradient elution. In either case, the TGF-β fraction is collected for further purification as described below.

Suitable cation exchange matrices include a wide variety of resins derivatized with cationic functionalities which are able to bind the anionic regions of TGF-β. Preferred are synthetic resins, such as styrene-divinylbenzene beads, derivatized with cationic functionalities such as carboxyl, carboxymethyl, sulfonyl, phosphoryl, and the like. Particularly useful are relatively weak resins, such as those having carboxyl or carboxy methyl functionalities. A particularly preferred resin is Baker Widepore CBX (40 μm bead size), commercially available from J. T. Baker.

The binding and elution conditions will vary depending on the binding strength of the cationic resin. For weak cationic resins, such as Baker Widepore CBX, binding may be effected at low ionic strength under slightly acidic conditions, typically pH 5–7, preferably about 6. After washing the matrix, the TGF-β may be selectively eluted by exposing the matrix to a mobile phase having an elevated ionic strength, employing either linear or step-wise elution. For the Baker Widepore CBX resin, TGF-β will elute at a pH of about 6 with a salt concentration between about 400 mM and 800 mM NaCl. The column may then be stripped and regenerated for subsequent use.

With the preferred Baker Widepore CBX matrix, the resin will initially be equilibrated with a buffer of 50 to 100 mM sodium acetate, 0.5% Tween 80, at pH 6. Buffer is applied to the column at a flow rate of 0.1 to 0.5 column volumes per minute until the pH stabilizes at 6. The conditioned media containing activated TGF-β is then applied to the column, typically using a gear pump, at a flow rate from about 0.5 to 1.0 column volumes per minute. A filter is provided to remove particulates which might plug the column matrix. The column matrix is then re-equilibrated with the equilibration buffer until the pH stabilizes at 6, typically requiring from about 5 to 8 column volumes. A wash buffer containing 100 mM sodium acetate, 300 mM NaCl, and 0.05% Tween 80 at pH 6 is next applied to the column at from about 0.1 to 0.2 column volumes per minute until the pH stabilizes at 6. A second buffer having 100 mM sodium acetate, 400 mM NaCl, 0.05% Tween 80, at pH 6 can be next applied to the column in a similar manner. TGF-β is then eluted from the column using an elution buffer containing 100 mM sodium acetate, 800 mM NaCl, 0.05% Tween 80, also at pH 6. The elution buffer is run until the buffer is apparently free from protein. A stripping buffer containing 200 mM sodium acetate and 40% ethanol, pH 6, is then applied to the column in order to regenerate the matrix. The storage buffer is the same as the resuspension buffer.

13. Nucleic Acid Separation

According to the present invention, a novel method for separating nucleic acids from protein-nucleic acid complexes is provided. While this method finds particular application in the purification of TGF-β, it is expected to be widely applicable to a variety of other recombinantly produced proteins, such as tissue plasminogen activator.

In general, the method relies on binding the protein-nucleic acid complex of interest to a cation exchange matrix of the type described above, preferably a strong cation exchange resin, more preferably having a high ligand density. The binding is achieved at a relatively low pH depending on the particular protein involved. Usually, the pH will be below 7, more usually being below about 6. The binding is performed under conditions of low or moderate ionic strength. The cation matrix (negatively-charged) will be able to bind both free protein (i.e., unassociated with DNA) and DNA-protein complexes, with binding occurring through the protein which is positively charged at the selected pH. The DNA, with a pH of about 2.5, will be unable to bind the cation matrix under the binding conditions.

After binding, the matrix is exposed to a mobile phase having an increased pH and substantially the same or a slightly increased ionic strength. The increase in pH or ionic strength tends to decrease the ionic traction between the protein and the nucleic acid, while having a minimum effect on the protein binding to the cationic resin. The higher pH value decreases the amount of positive and increases the amount of negative charge on the protein thus, decreasing the positively charged sites which are available to interact with the nucleic acids. In order for the method to work, the ion exchange resin must have a sufficient apparent ligand density to be able to compete with the DNA for the positively charged sites on the protein. The ionic strength of the mobile phase must be sufficiently low to minimize potential non-ionic secondary interactions between the protein being bound and the DNA, e.g., hydrophobic interactions.

In the purification of TGF-β, the nucleic acid separation step may be performed simultaneously with binding of the TGF-β to the cation exchange matrix described in Section 12 above. The TGF-β is loaded on the column at about pH 6, where the negatively charged sites on the matrix are able to preferentially bind the protein relative to the DNA. Free DNA is unable to bind at all to the column under these conditions. By slightly increasing the ionic strength, e.g., to about 300 mM, after binding is completed, the DNA remaining in the complexes is substantially removed.

14. Hydrophobic Interaction Chromatography

The TGF-β fraction collected from the cation exchange matrix (with or without nucleic acid removal) is next applied to a hydrophobic interaction matrix (usually in the form of a column) under conditions which allow binding of the TGF-β to the matrix, typically low ionic strength and low pH. The TGF-β is then selectively eluted by increasing the ionic strength of a mobile phase applied to the column, typically using a linear gradient. The TGF-β fraction is collected for concentration as described hereinbelow.

Suitable hydrophobic interaction matrices include a wide variety of uncharged resins having covalently attached hydrophobic groups, such as propyl, butyl, octal, phenyl, and the like. The resins may be cross-linked organic polymers, such as styrene-divinylbenzene or any one of a wide variety of other suitable particulate supports. A particularly preferred resin is Baker Widepore C4 (40 μm beads) derivatized with butyl and available from J. T. Baker.

Binding to the hydrophobic interaction column is effected under conditions of low ionic strength, usually at an acidic pH from 2 to 3, more usually about 2.5. Substantially all the protein in the TGF-β fraction from the ion exchange resin is bound to the column, and the proteins may be selectively eluted based on the differing strengths of hydrophobic interaction with the hydrophobic groups on the matrix, i.e. in order of increasing hydrophobicity of the protein. Elution may be performed with a step-wise or linear gradient, usually with a salt or alcohol eluant, preferably alcohol.

With the preferred Baker Widepore C4 matrix, equilibration may be performed with a buffer having 50 mM glycine, 30% ethanol, at a pH of 2.5. The matrix is loaded with the TGF-β fraction from the ion exchange column, and then re-equilibrated with the equilibration buffer described above. Proteins are then selectively eluted with an elution buffer mixture having an ethanol concentration increasing from about 30% to about 45%. The TGF-β adsorbs at approximately the midpoint of the gradient. The matrix is not reusable.

15. Multistage Concentration

The TGF-β product eluted from the hydrophobic interaction column has a very high product purity, typically at least about 95%, and preferably 99% or greater. The pure TGF-β product may then be concentrated by conventional protein concentration methods, such as ultrafiltration and passage through a sizing column. In the exemplary embodiment, the TGF-β from the hydrophobic interaction matrix is first ultrafiltration system followed by passage through a sizing column. Product from the sizing column is passed through a second stage of ultrafiltration and finally through a stage of sterile filtration to assure the sterility of the product. Product may then be stored in its concentrated form at a low temperature, typically from about 2° to 7° C., for a period of several months.

16. Purified TGF-β1 Compositions

An assay for TGF-β1 activity is based on the inhibition of $H^3$-uptake in Mink Lung epithelial cells (available from the Americal Tissue Culture Collection, Rockville, Md., USA, accession no. CCL 64. The cells are maintained in Eagle's Minimum Essential Medium (EMEM) (Gibco) supplemented with 10% fetal bovine serum (FBS) (Biofluids), streptomycin (200 μg/ml) and penicillin (200 U/ml). The cells are grown in 75 cm² tissue culture flasks to confluency and then are trypsinized (trypsin/EDTA, Gibco). Trypsinized cells are plated at about $5 \times 10^4$ cells/well in a culture plate (Costar). After again reaching confluency, the growth media is replaced with 0.5 ml of EMEM containing 1% FBS and antibiotics. After incubating for 24 hr at 37° C., test samples containing TGF-β1 are added to the growth medium and incubated for another 18 hr. After adding $H^3$-thymidine (approx. 2 μCi) to the test wells, incubation is continued for another 4 hr. Media are then removed and the wells washed once with 0.15M NaCl followed by cold 10% TCA precipitation. The resulting pellets are then washed three times with cold distilled water, lysed with 500 μL 1% SDS, and then counted.

Specific activity is determined by plotting CPM against the concentration of TGF-β1 (ng/ml). The inhibitory effect activity of each sample is expressed as 50% effective dose ($ED_{50}$). A unit of activity is defined as the amount of TGF-β1 that can inhibit the growth of the Mink Lung epithelial cells by 50%.

Preferred TGF-β1 compositions purified by the method of the present invention will have a specific activity (measured as just described) of at least $10^7$ U/mg, preferably being at least $1.5 \times 10^7$ U/mg, and more preferably being at least $2 \times 10^7$ U/mg.

Although the foregoing invention has been described in detail for purposes of clarity of understanding, it will be obvious that certain modifications may be practiced within the scope of the appended claims.

What is claimed is:

1. A method for separating nucleic acids from protein-nucleic acid complexes, said method comprising:

applying the protein-nucleic acid complexes to a cationic matrix under conditions of pH and ionic strength selected to promote selective binding of the complexes to the matrix; and increasing the matrix pH while maintaining or slightly increasing the ionic strength, whereby nucleic acids are released from the protein-nucleic acid complexes while the proteins remain bound to the cationic matrix.

2. A method as in claim 1, wherein the cation exchange matrix has an exchange functionality selected from the group consisting of carboxyl, carboxymethyl, sulfonyl, and phosphoryl.

3. A method as in claim 1, wherein the protein-nucleic acid complexes are applied to the cationic matrix at a pH from about 5 to 6.

4. A method as in claim 3, wherein the nucleic acids are released by maintaining the matrix pH to the range from about 5 to 6 while increasing the sodium chloride concentration to about 300 mM.

5. A method as in claim 1, further comprising adjusting the ionic strength of the matrix ionic strength to release the protein from the matrix and collecting the released protein.

* * * * *